United States Patent
Li et al.

(10) Patent No.: US 10,416,169 B2
(45) Date of Patent: Sep. 17, 2019

(54) PROTEIN ASSAY METHOD

(71) Applicant: North China University of Science and Technology, Tangshan (CN)

(72) Inventors: Hongxia Li, Tangshan (CN); Yuhan Luo, Tangshan (CN); Fuyuan Cao, Tangshan (CN); Huiyi Zhang, Tangshan (CN); Jinshan Hu, Tangshan (CN); Junjie Zhang, Tangshan (CN)

(73) Assignee: NORTH CHINA UNIVERSITY OF SCIENCE AND TECHNOLOGY, Tangshan (CN)

( * ) Notice: Subject to any disclaimer, the term of this patent is extended or adjusted under 35 U.S.C. 154(b) by 85 days.

(21) Appl. No.: 15/691,704

(22) Filed: Aug. 30, 2017

(65) Prior Publication Data
US 2018/0067123 A1    Mar. 8, 2018

(30) Foreign Application Priority Data
Sep. 2, 2016    (CN) .......................... 2016 1 0830958

(51) Int. Cl.
*G01N 33/68*    (2006.01)

(52) U.S. Cl.
CPC ..... *G01N 33/6806* (2013.01); *G01N 33/6827* (2013.01)

(58) Field of Classification Search
CPC ............... G01N 33/68; G01N 33/6806; G01N 33/6827; Y10T 436/25; Y10T 436/25375; Y10T 436/255; Y10T 436/25625
USPC ... 436/86, 89, 147, 161, 174, 177, 178, 179; 422/70, 527, 534
See application file for complete search history.

(56) References Cited

U.S. PATENT DOCUMENTS

| | | | | |
|---|---|---|---|---|
| 2,685,601 | A * | 8/1954 | Buck | A23J 3/32 530/343 |
| 2,991,309 | A * | 7/1961 | Hoglan | A23J 3/32 426/656 |
| 3,952,109 | A * | 4/1976 | Rao | A23L 27/215 426/48 |
| 4,874,893 | A * | 10/1989 | Flork | C07C 227/28 562/443 |
| 2003/0010620 | A1 * | 1/2003 | Izatt | C07K 1/12 204/157.61 |
| 2005/0002962 | A1 * | 1/2005 | Pasco | A61K 36/07 424/195.15 |
| 2009/0035399 | A1 * | 2/2009 | Hettiarachchy | A23C 9/1307 424/750 |

OTHER PUBLICATIONS

Serlupi Crescenzi, G. et al (abstract), Rivista di Scienza e Technologia degli Alinnenti e di Nutrizione Unnana, vol. 5(2), 1975, pp. 89-90.*

* cited by examiner

*Primary Examiner* — Maureen Wallenhorst
(74) *Attorney, Agent, or Firm* — Matthias Scholl P.C.; Matthias Scholl

(57) ABSTRACT

A protein assay method, including: 1) dissolving 4-hydroxybenzenesulfonic acid in an ethanol, methanol, or acetonitrile aqueous solution to prepare a hydrolysis reagent, adding a protein sample and the hydrolysis reagent to a hydrolysis tube, and uniformly mixing the protein sample and the hydrolysis reagent, charging argon or nitrogen into the hydrolysis tube to remove dissolved oxygen, sealing and drying the hydrolysis tube, and hydrolyzing the protein sample; 2) cooling the hydrolysis tube to room temperature, filtering and adding a resulting hydrolysate to a volumetric flask, washing the hydrolysis tube and a filter paper, collecting and adding a resulting washing solution to the volumetric flask to a constant volume; 3) drawing a hydrolysate solution from the volumetric flask, completely drying the hydrolysate solution to yield a solid product; and 4) diluting the solid product using a diluent, and analyzing amino acids of the solid product.

4 Claims, 6 Drawing Sheets

PROTEIN ASSAY METHOD

CROSS-REFERENCE TO RELATED APPLICATIONS

Pursuant to 35 U.S.C. § 119 and the Paris Convention Treaty, this application claims foreign priority to Chinese Patent Application No. 201610830958.2 filed Sep. 2, 2016, the contents of which are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, and Cambridge, Mass. 02142.

BACKGROUND OF THE INVENTION

Field of the Invention

The invention relates to a protein assay method.

Description of the Related Art

Protein assay methods include the Kjeldahl method, the Biuret method, the Lowry protein assay, the ultraviolet absorption method and the Coomassie brilliant blue method. However, the methods cannot differentiate protein nitrogen from non-protein nitrogen accurately.

Hydrolyzing proteins into amino acids and then analyzing the amino acids can learn the varieties and concentrations of the amino acids which constitute the proteins and evaluate the protein quality.

Conventional protein hydrolysis methods include acid hydrolysis method, alkaline hydrolysis method and enzyme hydrolysis method. The acid hydrolysis method damages tryptophan, decomposes a small amount of hydroxy-aminoacid (serine and threonine) and deaminates asparagine and glutamine. The alkaline hydrolysis method racemizes amino acids and deaminates arginine to produce ornithine and urea. The enzyme hydrolysis method requires a plurality of enzymes to hydrolyze proteins, and therefore, it is costly and inefficient.

SUMMARY OF THE INVENTION

In view of the above-described problems, it is one objective of the invention to provide a protein assay method. The method comprises hydrolyzing proteins into amino acids and measuring the protein concentration by amino acid analysis.

To achieve the above objective, in accordance with one embodiment of the invention, there is provided a protein assay method, the method comprising:

1. Preparation of Hydrolysis Reagent and Hydrolysate Diluent (1) Prepare a Hydrolysis Reagent Weigh out and add 17-35 g of hydroxybenzenesulfonic acid to a 50-mL small beaker. Dissolve the hydroxybenzenesulfonic acid in an aqueous solution of ethanol, methanol or acetonitrile with the concentration of 10-30% (v/v) to produce 4-8 mol/L hydroxybenzenesulfonic acid solution in a 25 mL of volumetric flask.

(2) Prepare a Hydrolysate Diluent

Prepare and dissolve 13.50 g of sodium acetate ($CH_3COONa \cdot 3H_2O$), 35.00 mL of ethanol, 2.50 mL of formic acid, 5.00 mL of acetic acid and 14.75 mL of trifluoroacetic acid in water in a 200-mL beaker. Then transfer the mixture to get a 500 mL of a hydrolysate diluent.

2. Protein Hydrolysis (1) Hydrolysis of Protein Sample: dissolving 4-hydroxybenzenesulfonic acid in an ethanol, methanol, or acetonitrile aqueous solution to prepare a hydrolysis reagent, adding a protein sample and the hydrolysis reagent to a hydrolysis tube, and uniformly mixing the protein sample and the hydrolysis reagent through ultrasonic oscillation, charging argon or nitrogen into the hydrolysis tube to remove dissolved oxygen, sealing the hydrolysis tube and transferring the hydrolysis tube into a vacuum oven, and hydrolyzing the protein sample in the vacuum oven at a temperature of between 100 and 120° C. for between 14 and 20 hrs.

(2) Filtration and Constant Volume: cooling the hydrolysis tube to room temperature, filtering the mixture in the hydrolysis tube through a filter paper to obtain a filtrate comprising a hydrolysate, transferring the filtrate to a volumetric flask, washing the hydrolysis tube and the filter paper and collecting a resulting washing solution, transferring the resulting washing solution to the volumetric flask, and diluting the filtrate and the resulting washing solution to a volume marking of the volumetric flask.

(3) Drying of hydrolysates: drawing a hydrolysate solution from the volumetric flask obtained in (2), completely drying the hydrolysate solution in the vacuum oven at a temperature of between 40 and 60° C. to yield a solid product.

3. Measurement of Amino Acids (1) The Amino Acid Analysis Principle: based on the different acid-base properties, polarities and relative molecular masses of amino acids, the cation exchange column of the amino acid analyzer can separate various amino acids on the chromatographic column. The sequence of amino acids eluted by buffer solution is acidic amino acids, amino acids with large polarities, non-polar amino acids and basic amino acid. The eluted amino acids realize chromogenic reactions with ninhydrin. The color shades and the content of amino acids present a linear relation. Then, the spectrophotometry is used to assay amino acids. Every eluted amino acid corresponds to a different retention time. The retention time of the obtained chromatogram can be used to carry out qualitative analysis of amino acids. The area and height of every chromatogram peak can be used to carry out quantitative analysis of amino acids.

(2) Analysis of the Standard Amino Acid Sample

The Standard Amino Acid Sample 1: the standard amino acid sample contains 19 amino acids which are cysteine (Cys), aspartic acid (Asp), methionine sulfone (MetSON), threonine (Thr), serine (Ser), glutamic acid (Glu), proline (Pro), glycine (Gly), alanine (Ala), cystine ($(Cys)_2$), valine (Val), methionine (Met), isoleucine (Ile), leucine (Leu), tyrosine (Tyr), phenylalanine (Phe), histidine (His), lysine (Lys) and arginine (Arg). The concentration of every amino acid in the standard sample is 100 nmol/mL. The chromatogram of the standard sample 1 is shown in FIG. 1.

The Standard Amino Acid Sample 2: the concentration of tryptophan (Trp) is 100 nmol/mL. The chromatogram of the standard sample 2 is shown in FIG. 2.

A300 amino acid analyzer of German aminoSys is adopted. The sample amount is 20 µL. The amount of every amino acid participating in the chromogenic reaction is 2 nmol.

(3) The Amino Acid Analysis and Protein Concentration Computing of the Sample

Add the hydrolysate diluent to the dried sample hydrolysate tube. Put the tube on an oscillating mixer and blend the mixture evenly. Draw a small amount of the mixture by using a syringe. Use a filter to filter the mixture. Use the A300 amino acid analyzer to analyze amino acids of the hydrolysate. The sample amount is 20 μL. The amino acid chromatogram of the sample is obtained. Compare the amino acid chromatogram of the sample with the amino acid chromatogram of the standard samples. Calculate the varieties and contents of amino acids in the sample according to the retention time and each peak area on the chromatogram of the sample.

According to the ratio of the peak area of the sample to the peak area of the standard sample, get the mole number of each amino acid in the hydrolysate. The formula is:

$$n_i = \frac{S_i}{S_0} \times 2 \times 50 / 0.02 \times 10^{-9} \quad (1)$$
$$n_i = \frac{S_i}{S_0} \times 5 \times 10^{-6}$$

$n_i$—a mole number of amino acids in the sample;
$S_i$—a peak area of every amino acid in the sample;
$S_0$—a peak area of amino acids in the standard sample;
2—a nanomole number of amino acids in the sample, nmol;
0.02—the sample amount, mL; and
50—the dilution factor of the sample.
The mass of every amino acid in the sample:

$$m_i = n_i \times M_i \quad (2)$$

$m_i$—a mass of every amino acid, g; and
$M_i$—a relative molecular mass of amino acids.

Protein hydrolysis is equivalent to adding a water molecule between two amino acids. Since proteins are macromolecular compounds, the molecular mass of protein is very high. Every protein comprises thousands of amino acids. Therefore, the mole number of amino acids minus the same mole number of water molecules is the mole number of proteins. The error caused by one water molecule between every protein chain can be ignored. The content percent of proteins in the sample is:

$$P = \left(\sum_i m_i - \sum n_i \times M_{H_2O}\right) / m \times 100\% \quad (3)$$

$m_i$—a mass of every amino acid, g;
$n_i$—a mole number of amino acids in the sample, mol;
$M_{H_2O}$—a relative molecular mass of water; and
m—a mass of weighed sample, g.

Advantages of the protein assay method according to embodiments of the invention are summarized as follows:

1) The protein hydrolysis reagent adopted by the invention is benzenesulfonic acid. Compared to traditional hydrolysis reagents which are hydrochloric acid or sodium hydroxide, benzenesulfonic acid is mild and does not damage tryptophan.

2) The hydroxybenzenesulfonic acid hydrolysis reagent is prepared by an aqueous solution of ethanol, methanol or acetonitrile, and reduces solution polarities. Compared to a traditional aqueous solution, the hydroxybenzenesulfonic acid hydrolysis reagent has a low polarity and protects the amino acids.

3) The method for protein hydrolysis does not damage amino acids. Therefore, the protein concentration can be measured by analyzing the amino acids.

4) As for foods, the protein concentration can be measured by variety and content analysis of the amino acids. Thus, the proportions of essential amino acids which constitute proteins can also be learned, which is favorable to nutritive value assessment of foods.

DETAILED DESCRIPTION OF THE EMBODIMENTS

For further illustrating the invention, experiments detailing a protein assay method are described hereinbelow combined with the drawings. It should be noted that the following examples are intended to describe and not to limit the invention.

EXAMPLE 1

1. Protein Hydrolysis of Sample: weigh out 0.2000 g of dried milk powder from the sample and put the 0.2000 g of dried milk powder into a hydrolysis tube. The sample is provided by Tangshan Product Quality Supervision and Inspection Institute and is a product of a milk enterprise obtained by drying fresh milk directly. Add 5 mL of p-4-hydroxybenzenesulfonic acid as a hydrolysis reagent with the concentration of 6 mol/L to the hydrolysis tube. The 4-hydroxybenzenesulfonic acid is prepared by ethanol solution with the concentration of 20%. The sample is blended evenly by ultrasound for 30 minutes. Remove dissolved oxygen by adding argon or nitrogen. Seal the tube and put the tube in a vacuum drying oven for hydrolysis at 110° C. for 17 hours. After hydrolysis, take out the hydrolysis tube and cool the hydrolysis tube to room temperature. After opening the tube, filter the hydrolysate to a 50 mL volumetric flask. Wash the hydrolysis tube and the filter paper by water. Collect a cleaning solution and get a constant-volume sample. Draw 1 mL of the constant-volume sample and put the 1 mL sample in a vacuum drying oven to dry the sample completely at 50° C. A few solids or vestiges are left at the bottom of the tube.

Figure 1:
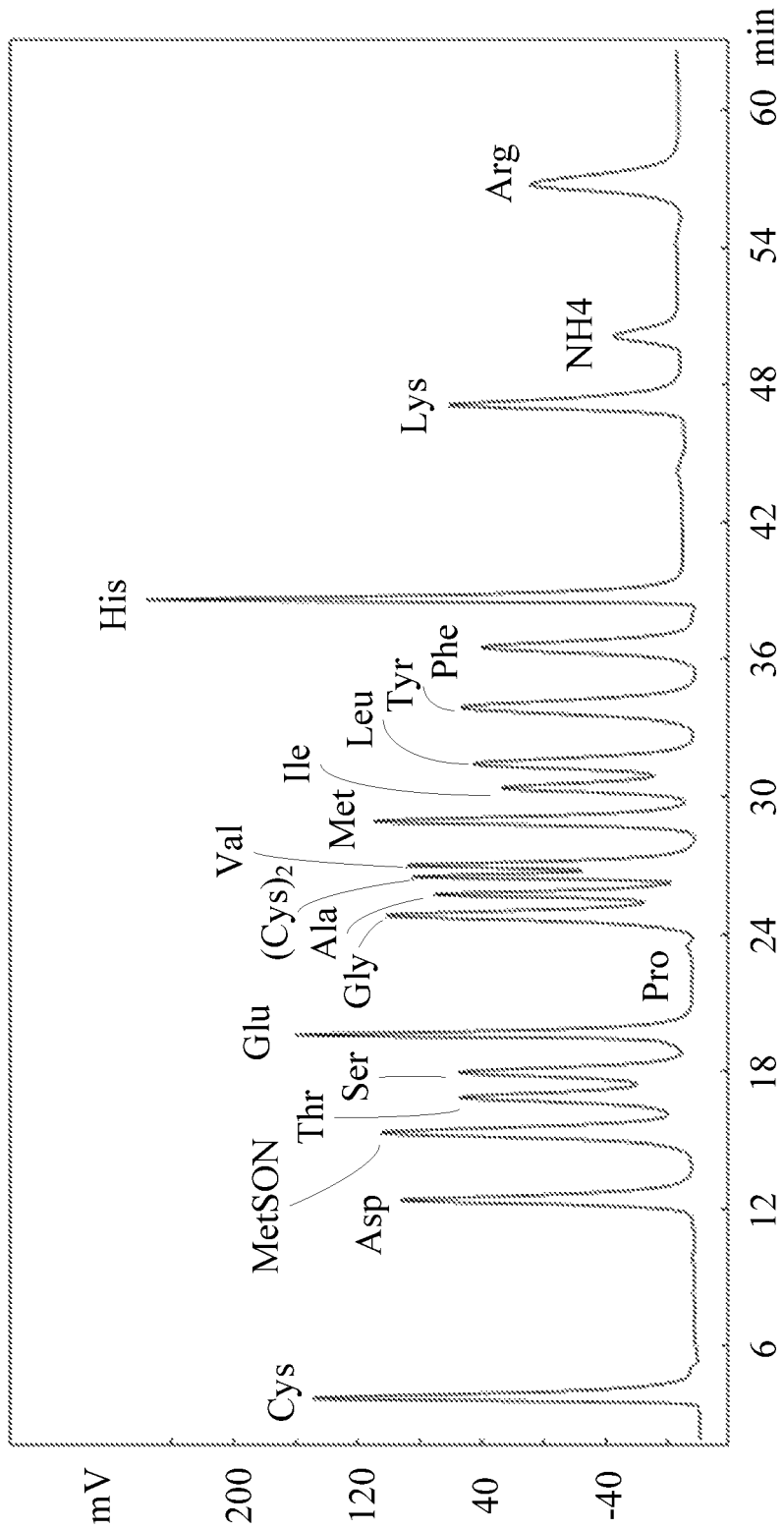
FIG. 1 is an amino acid chromatogram of a standard sample 1.
Figure 2:
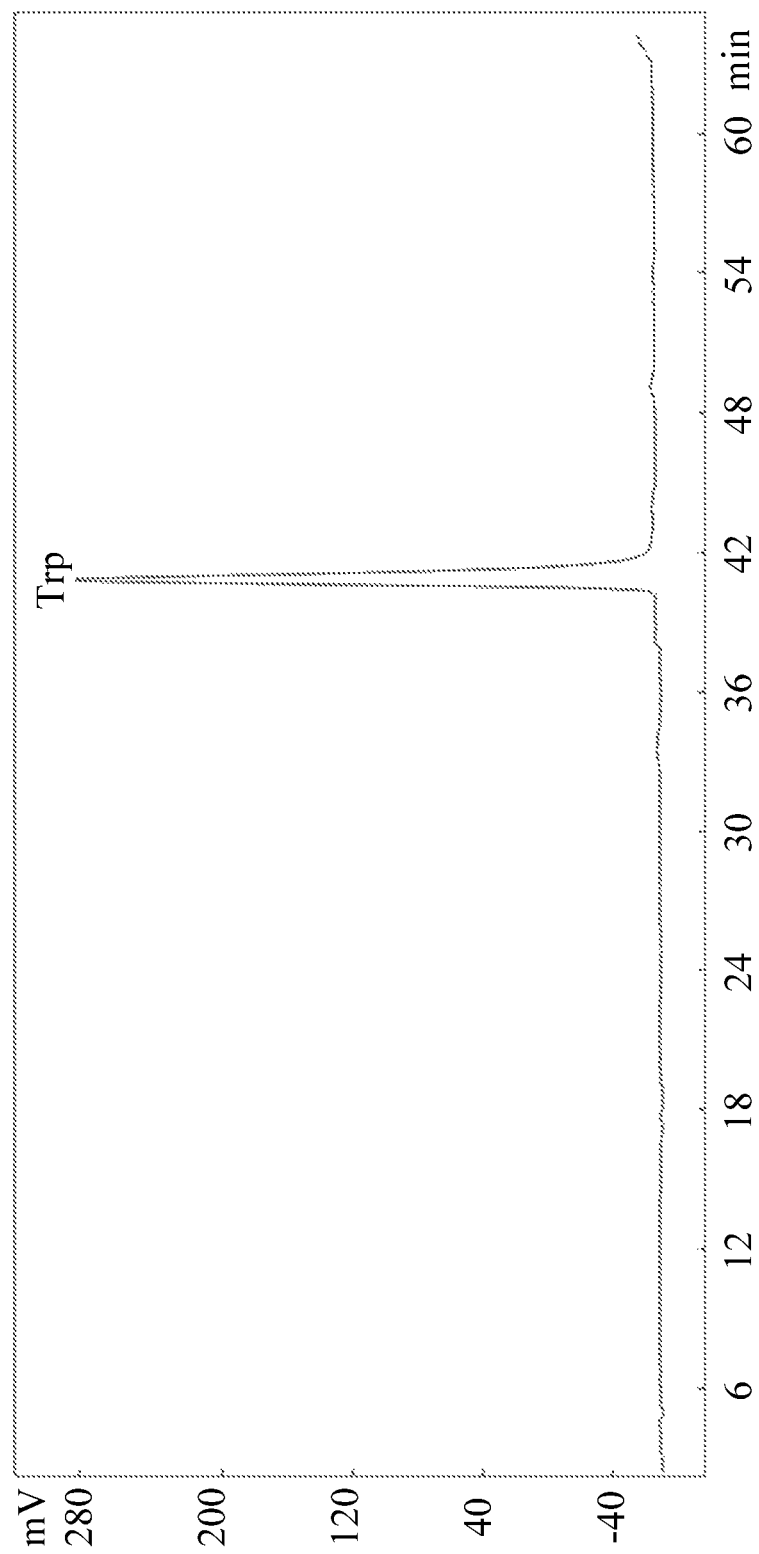
FIG. 2 is an amino acid chromatogram of a standard sample 2.
Figure 3:
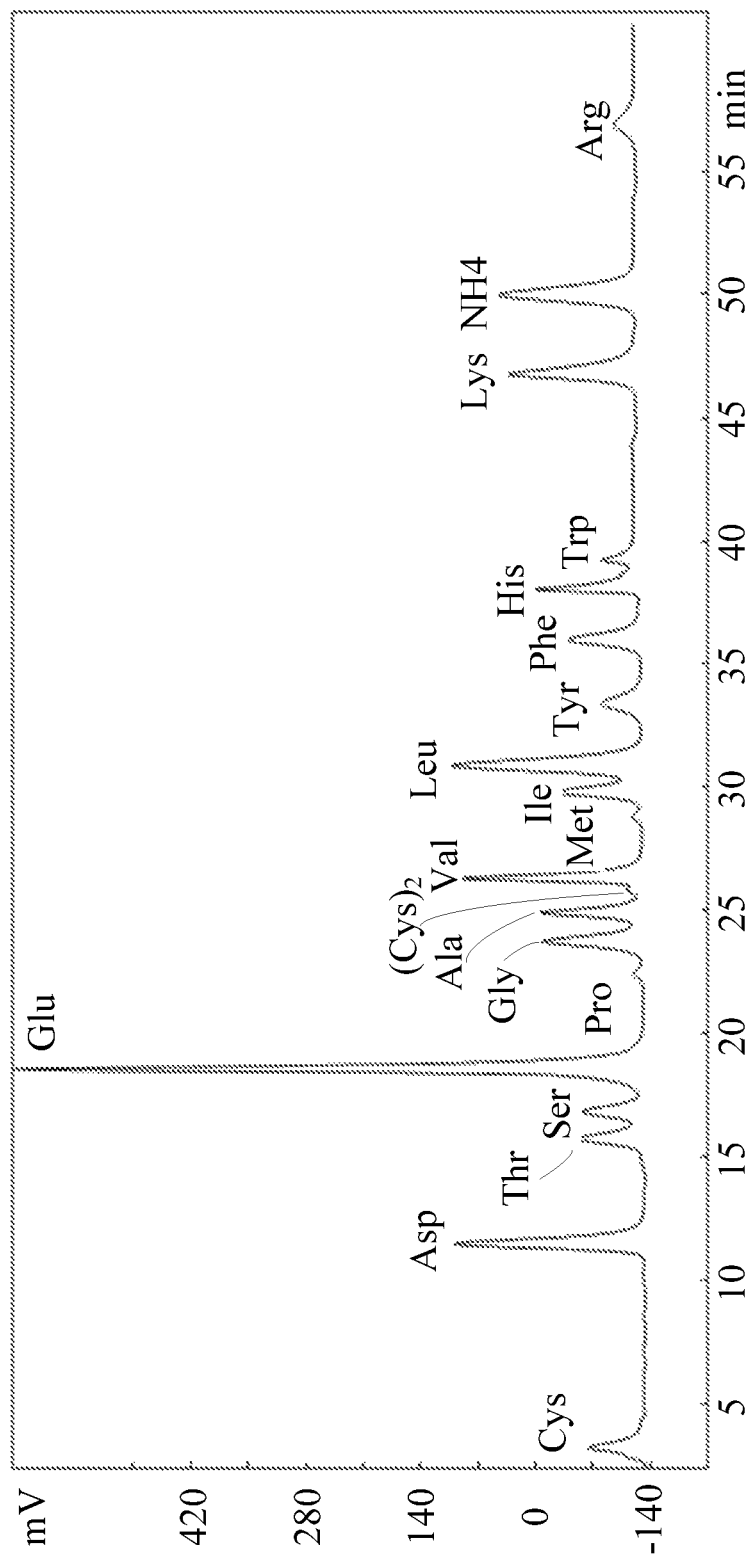
FIG. 3 is an amino acid chromatogram of dried milk powder hydrolyzed by 4-hydroxybenzenesulfonic acid in accordance with one embodiment of the invention.

2. Amino Acid Analysis: add 1 mL of a sample diluent to the hydrolysate tube comprising the dried sample. Put the hydrolysate tube on an oscillating mixer for blending the mixture evenly. Draw a small amount of the mixture by using a syringe. After filtration, use the A300 amino acid analyzer to analyze the amino acids of the hydrolysate. The sample amount is 20 μL. The amino acid chromatogram No. 3 of the sample is shown in FIG. 3. Compare the amino acid chromatogram No. 3 of the sample with the amino acid chromatograms 1 and 2 of the standard sample. Table 1 shows the varieties and contents of amino acids in the sample according to the retention time and each peak area thereof on the chromatogram of the sample.

TABLE 1

Amino acid analysis data of dried milk powder hydrolyzed by 4-hydroxybenzenesulfonic acid

| Amino Acid | Molecular Mass | Mole Number μmol | Mass μg |
|---|---|---|---|
| Cys | 121.2 | 0.3653 | 44.27 |
| Asp | 133.1 | 164.9 | 21950 |
| MetSON | 181.2 | 0 | 0 |
| Thr | 119.1 | 22.68 | 2701 |
| Ser | 105.1 | 28.99 | 3047 |
| Glu | 147.1 | 46.41 | 6827 |
| Pro | 115.1 | 25.46 | 2930 |
| Gly | 75.1 | 7.906 | 593.8 |
| Ala | 89.1 | 12.09 | 1077 |
| (Cys)$_2$ | 240.3 | 0.8829 | 212.2 |
| Val | 117.1 | 22.13 | 2591 |
| Met | 149.2 | 4.775 | 712.4 |
| Ile | 131.2 | 9.986 | 1310 |
| Leu | 131.2 | 20.8 | 2729 |
| Tyr | 181.2 | 7.55 | 1368 |
| Phe | 165.2 | 8.444 | 1395 |
| His | 155.2 | 9.592 | 1489 |
| Trp | 204.2 | 7.158 | 1462 |
| Lys | 146.2 | 10.57 | 1546 |
| Arg | 174.2 | 5.753 | 1002 |

The total mole number of the amino acids is 416.4 μmol. The total mass of the amino acids is 54990 μg. The content percent of proteins in the sample is 23.74%.

Figure 4:
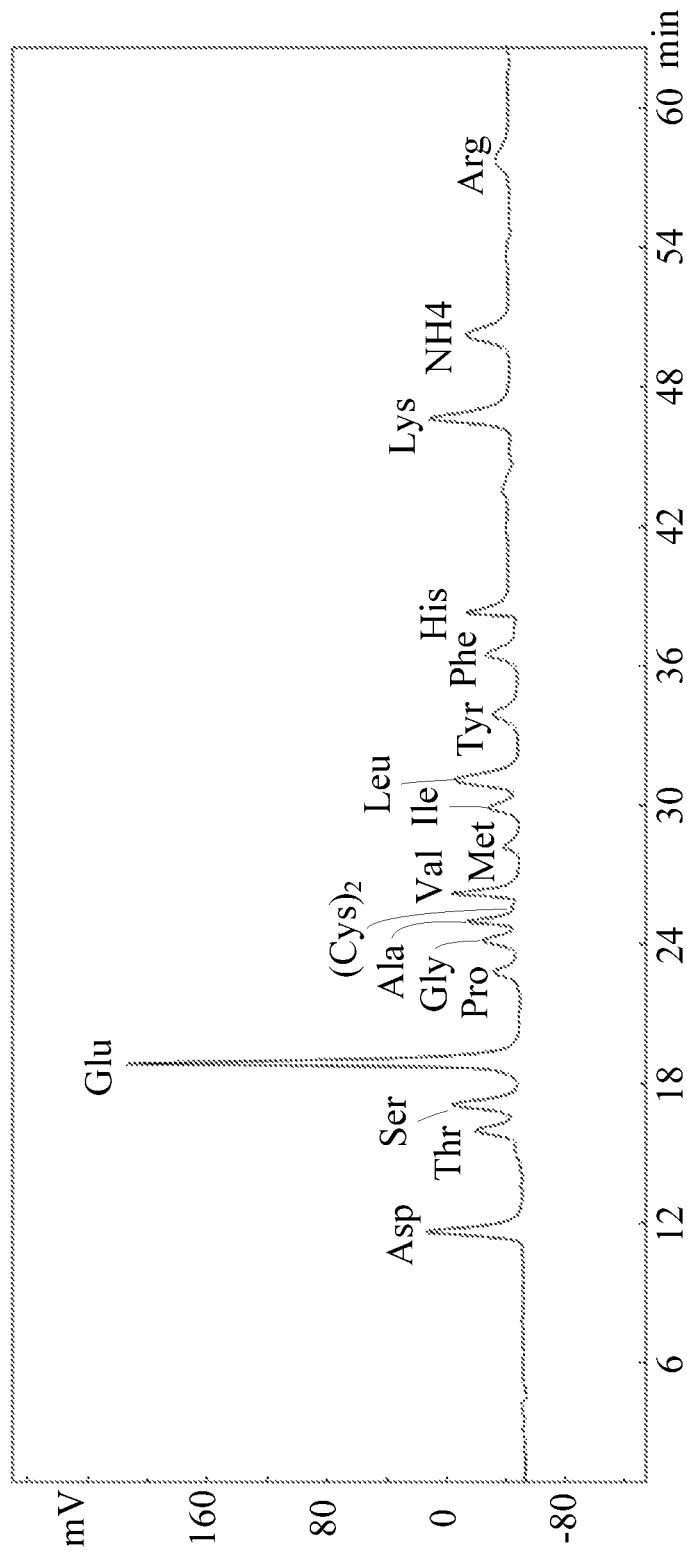
FIG. 4 is an amino acid chromatogram of dried milk powder hydrolyzed by hydrochloric acid in accordance with one embodiment of the invention.

3. Contrast Experiment: weigh out 0.2000 g of dried milk powder from the aforesaid sample and put the dried milk powder into a hydrolysis tube. Use 5 mL of hydrochloric acid with the concentration of 6 mol/L as a hydrolysis reagent to hydrolyze the sample at 110° C. for 24 hours. The other steps are the same with the steps 1 and 2. Amino acid analysis is carried out to get a chromatogram as shown in FIG. 4. Table 2 shows the varieties and contents of amino acids in the sample according to the retention time and each peak area thereof on the chromatogram of the sample.

TABLE 2

Amino acid analysis data of dried milk powder hydrolyzed by hydrochloric acid

| Amino Acid | Molecular Mass | Mole Number μmol | Mass μg |
|---|---|---|---|
| Cys | 121.2 | 0 | 0 |
| Asp | 133.1 | 163.7 | 21790 |
| MetSON | 181.2 | 0 | 0 |
| Thr | 119.1 | 12.9 | 1536 |
| Ser | 105.1 | 15.34 | 1612 |
| Glu | 147.1 | 31.04 | 4566 |
| Pro | 115.1 | 19.71 | 2268 |
| Gly | 75.1 | 4.746 | 356.4 |
| Ala | 89.1 | 6.848 | 610.1 |
| (Cys)$_2$ | 240.3 | 0.7923 | 190.4 |
| Val | 117.1 | 7.14 | 836.1 |
| Met | 149.2 | 2.07 | 308.81 |
| Ile | 131.2 | 5.352 | 702.2 |
| Leu | 131.2 | 10.42 | 1367 |
| Tyr | 181.2 | 2.75 | 498.4 |
| Phe | 165.2 | 4.018 | 6638 |
| His | 155.2 | 3.704 | 574.9 |
| Trp | 204.2 | 0 | 0 |
| Lys | 146.2 | 7.015 | 1026 |
| Arg | 174.2 | 2.439 | 424.9 |

The total mole number of the amino acids is 300.2 μmol. The total mass of the amino acids is 39340 μg. The content percent of proteins in the sample is 16.97%. Compared to 4-hydroxybenzenesulfonic acid, the hydrolysate of hydrochloric acid as a hydrolysis reagent does not contain tryptophan and cysteine but the hydrolysate of 4-hydroxybenzenesulfonic acid contains tryptophan and cysteine. It means hydrochloric acid as the hydrolysis reagent damages tryptophan and cysteine completely. In addition, the protein concentration is 16.97% when hydrochloric acid is used as a hydrolysis reagent; and the protein concentration is 23.74% when 4-hydroxybenzenesulfonic acid is used as a hydrolysis reagent. The protein concentration and the amino acid content obtained with 4-hydroxybenzenesulfonic acid as a hydrolysis reagent is higher than that with hydrochloric acid as a hydrolysis reagent. It means that hydrochloric acid as a hydrolysis reagent damages amino acids obviously.

EXAMPLE 2

1. Protein Hydrolysis of Sample: weigh out 0.2000 g of commercial milk powder and put the 0.2000 g of dried milk powder into a hydrolysis tube. Add 6 mL of p-4-hydroxybenzenesulfonic acid as a hydrolysis reagent with the concentration of 5.5 mol/L to the hydrolysis tube. The 4-hydroxybenzenesulfonic acid is prepared by acetonitrile solution with the concentration of 20%. The sample is blended evenly by ultrasound for 25 minutes. Remove dissolved oxygen by adding argon or nitrogen. Seal the tube and put the tube in a vacuum drying oven for hydrolysis at 105° C. for 20 hours. After hydrolysis, take out the hydrolysis tube and cool the hydrolysis tube to room temperature. After opening the tube, filter the hydrolysate to a 50-mL volumetric flask. Wash the hydrolysis tube and the filter paper by water. Collect a cleaning solution and get a constant-volume sample. Draw 1 mL of the constant-volume sample and put the 1 mL sample in a vacuum drying oven to dry the sample completely at 55° C. A few solids or vestiges are left at the bottom of the tube.

Figure 5:
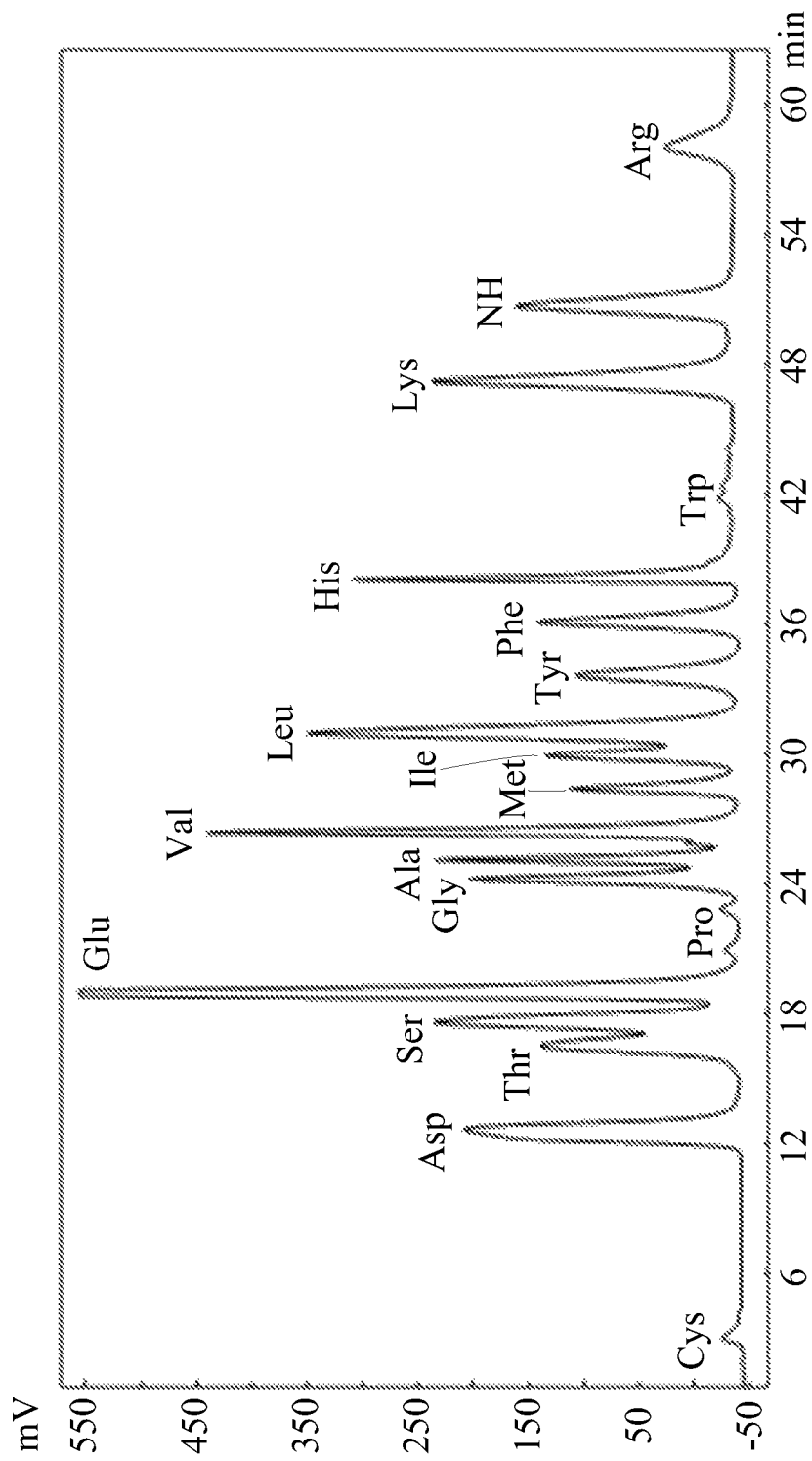
FIG. 5 is an amino acid chromatogram of commercial milk powder hydrolyzed by 4-hydroxybenzenesulfonic acid in accordance with one embodiment of the invention.

2. Amino Acid Analysis: add 1 mL of a sample diluent to the hydrolysate tube comprising the dried sample. Put the hydrolysate tube on an oscillating mixer for blending the mixture evenly. Draw a small amount of the mixture by using a syringe. After filtration, use the A300 amino acid analyzer to analyze the amino acids of the hydrolysate. The sample amount is 20 μL. The amino acid chromatogram No. 5 of the sample is shown in FIG. 5.

3. Calculating the protein concentration: Compare the amino acid chromatogram No. 5 of the sample with the amino acid chromatograms 1 and 2 of the standard sample. Table 3 shows the varieties and contents of amino acids in the sample according to the retention time and each peak area thereof on the chromatogram of the sample.

TABLE 3

Amino acid analysis data of commercial milk powder hydrolyzed by 4-hydroxybenzenesulfonic acid

| Amino Acid | Molecular Mass | Mole Number μmol | Mass μg |
|---|---|---|---|
| Cys | 121.2 | 1.185 | 143.6 |
| Asp | 133.1 | 33.45 | 44516 |
| MetSON | 181.2 | 0 | 0 |
| Thr | 119.1 | 19.67 | 23426 |
| Ser | 105.1 | 27.74 | 29156 |
| Glu | 147.1 | 33.38 | 49106 |

TABLE 3-continued

Amino acid analysis data of commercial milk powder hydrolyzed by 4-hydroxybenzenesulfonic acid

| Amino Acid | Molecular Mass | Mole Number μmol | Mass μg |
|---|---|---|---|
| Pro | 115.1 | 41.43 | 47686 |
| Gly | 75.1 | 13.8 | 10366 |
| Ala | 89.1 | 19.18 | 17096 |
| (Cys)₂ | 240.3 | 0.6709 | 161.3 |
| Val | 117.1 | 31.37 | 3673 |
| Met | 149.2 | 8.484 | 1266 |
| Ile | 131.2 | 18.81 | 24676 |
| Leu | 131.2 | 38.97 | 5114 |
| Tyr | 181.2 | 12.24 | 2218 |
| Phe | 165.2 | 14.66 | 2422 |
| His | 155.2 | 12.486 | 19372 |
| Trp | 204.2 | 6.0186 | 1229 |
| Lys | 146.2 | 33.71 | 4928 |
| Arg | 174.2 | 8.448 | 1472 |

The total mole number of the amino acids is 375.7 μmol. The total mass of the amino acids is 49160 μg. The content percent of proteins in the sample is 21.20%. The sample contains relatively high content of tryptophan, which means the hydrolysis method of the present disclosure can protect tryptophan well.

EXAMPLE 3

1. Protein Hydrolysis of Sample: weigh out 0.2000 g of commercial infant formula milk powder and put the 0.2000 g of dried milk powder into a hydrolysis tube. Add 5 mL of p-4-hydroxybenzenesulfonic acid as a hydrolysis reagent with the concentration of 7 mol/L to the hydrolysis tube. The 4-hydroxybenzenesulfonic acid is prepared by methanol solution with the concentration of 25%. The sample is blended evenly by ultrasound for 30 minutes. Remove dissolved oxygen by adding argon or nitrogen. Seal the tube and put the tube in a vacuum drying oven for hydrolysis at 115° C. for 16 hours. After hydrolysis, take out the hydrolysis tube and cool the hydrolysis tube to room temperature. After opening the tube, filter the hydrolysate to a 50 mL volumetric flask. Wash the hydrolysis tube and the filter paper by water. Collect a cleaning solution and get a constant-volume sample. Draw 1 mL of the constant-volume sample and put the 1 mL sample in a vacuum drying oven to dry the sample completely at 48° C. A few solids or vestiges are left at the bottom of the tube.

Figure 6:
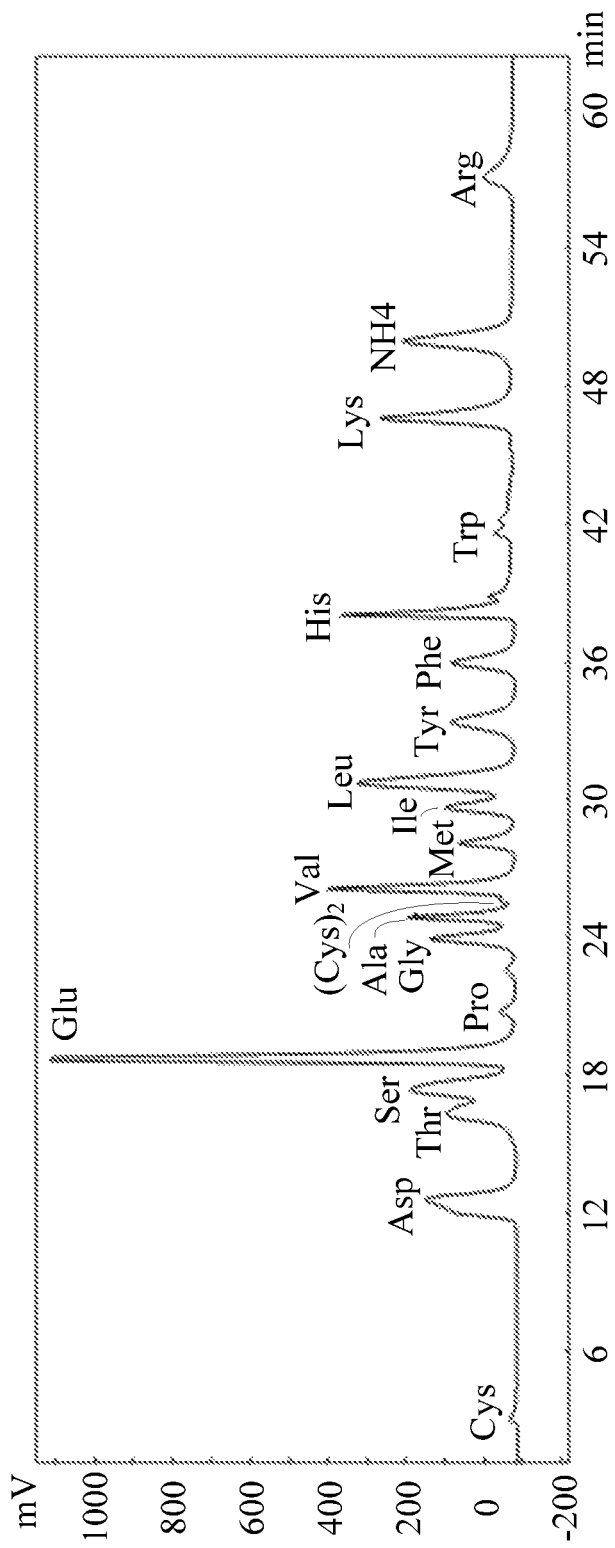
FIG. 6 is an amino acid chromatogram of commercial infant formula milk powder hydrolyzed by 4-hydroxybenzenesulfonic acid in accordance with one embodiment of the invention.

2. Amino Acid Analysis: add 1 mL of a sample diluent to the hydrolysate tube comprising the dried sample. Put the hydrolysate tube on an oscillating mixer for blending the mixture evenly. Draw a small amount of the mixture by using a syringe. After filtration, use the A300 amino acid analyzer to analyze the amino acids of the hydrolysate. The sample amount is 20 μL. The amino acid chromatogram No. 6 of the sample is shown in FIG. 6.

3. Calculating the protein concentration: Compare the amino acid chromatogram No. 6 of the sample with the amino acid chromatograms 1 and 2 of the standard sample. Table 4 shows the varieties and contents of amino acids in the sample according to the retention time and each peak area thereof on the chromatogram of the sample.

TABLE 4

Amino acid analysis data of commercial infant formula milk powder hydrolyzed by 4-hydroxybenzenesulfonic acid

| Amino Acid | Molecular Mass | Mole Number μmol | Mass μg |
|---|---|---|---|
| Cys | 121.2 | 0.42 | 50.89 |
| Asp | 133.1 | 8.90 | 1183.94 |
| MetSON | 181.2 | 0 | 0 |
| Thr | 119.1 | 10.46 | 1245.38 |
| Ser | 105.1 | 18.42 | 1935.52 |
| Glu | 147.1 | 12.30 | 1809.40 |
| Pro | 115.1 | 13.86 | 1595.12 |
| Gly | 75.1 | 5.04 | 378.20 |
| Ala | 89.1 | 7.01 | 624.94 |
| (Cys)₂ | 240.3 | 0.83 | 200.10 |
| Val | 117.1 | 23.28 | 2725.85 |
| Met | 149.2 | 1.34 | 200.64 |
| Ile | 131.2 | 7.89 | 1034.73 |
| Leu | 131.2 | 14.58 | 1913.16 |
| Tyr | 181.2 | 5.30 | 959.47 |
| Phe | 165.2 | 4.80 | 793.40 |
| His | 155.2 | 5.39 | 836.31 |
| Trp | 204.2 | 4.82 | 984.24 |
| Lys | 146.2 | 13.76 | 2012.24 |
| Arg | 174.2 | 5.42 | 944.98 |

The total mole number of the amino acids is 163.82 μmol. The total mass of the amino acids is 21428.51 μg. The content percent of proteins in the sample is 9.24%. The sample contains relatively high content of tryptophan, which means the hydrolysis method of the present disclosure can protect tryptophan well.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A protein assay method, comprising:
1) dissolving 4-hydroxybenzenesulfonic acid in an ethanol, methanol, or acetonitrile aqueous solution to yield a hydrolysis reagent, adding a protein sample and the hydrolysis reagent to a hydrolysis tube, and uniformly mixing the protein sample and the hydrolysis reagent by sonicating, charging argon or nitrogen into the hydrolysis tube to remove dissolved oxygen, sealing the hydrolysis tube and transferring the hydrolysis tube into a vacuum oven, and hydrolyzing the protein sample in the vacuum oven at a temperature of between 100 and 120° C. for between 14 and 20 hours to yield a mixture in the hydrolysis tube;
2) cooling the hydrolysis tube to room temperature, filtering the mixture in the hydrolysis tube through a filter paper to obtain a filtrate comprising a hydrolysate, transferring the filtrate to a volumetric flask, washing the hydrolysis tube and the filter paper and collecting a resulting washing solution, transferring the resulting washing solution to the volumetric flask, and diluting the filtrate and the resulting washing solution to a volume marking of the volumetric flask;
3) drawing a hydrolysate solution from the volumetric flask obtained in 2), completely drying the hydrolysate solution in the vacuum oven at a temperature of between 40 and 60° C. to yield a solid product; and

4) diluting the solid product using a diluent, analyzing amino acids of the solid product using an amino acid analyzer to obtain a chromatogram comprising peaks representing amino acids in the solid product, calculating concentrations of the amino acids of the solid product based on the peaks in the chromatogram, and calculating a protein concentration in the protein sample based on the concentrations of the amino acids of the solid product.

2. The method of claim 1, wherein a concentration of the 4-hydroxybenzenesulfonic acid in the hydrolysis reagent is between 4 and 8 mol/L.

3. The method of claim 1, wherein a concentration of the ethanol, methanol, or acetonitrile aqueous solution is between 10 and 30% (v/v).

4. The method of claim 1, wherein the diluent in 4) is prepared by mixing sodium acetate ($CH_3COONa3H_2O$), ethanol, formic acid, acetic acid and trifluoroacetic acid in water.

* * * * *